(12) United States Patent
Kabadayi

(10) Patent No.: US 11,622,755 B2
(45) Date of Patent: Apr. 11, 2023

(54) FIRST RESPONDER DEVICE

(71) Applicants: Cihan Kabadayi, Haar (DE); Berthold Lorenz, Villingen-Schwenningen (DE)

(72) Inventor: Cihan Kabadayi, Haar (DE)

(73) Assignees: Cihan Kabadayi, Haar (DE); Berthold Lorenz, Villingen-Schwenningen (DE)

( * ) Notice: Subject to any disclaimer, the term of this patent is extended or adjusted under 35 U.S.C. 154(b) by 975 days.

(21) Appl. No.: 16/348,907

(22) PCT Filed: Nov. 10, 2017

(86) PCT No.: PCT/EP2017/001314
§ 371 (c)(1),
(2) Date: May 10, 2019

(87) PCT Pub. No.: WO2018/086743
PCT Pub. Date: May 17, 2018

(65) Prior Publication Data
US 2019/0261965 A1 Aug. 29, 2019

(30) Foreign Application Priority Data
Nov. 10, 2016 (DE) .................... 10 2016 222 125.6

(51) Int. Cl.
*A61B 17/00* (2006.01)
*A61F 7/12* (2006.01)
(Continued)

(52) U.S. Cl.
CPC .......... *A61B 17/0057* (2013.01); *A61F 7/123* (2013.01); *A61F 13/00021* (2013.01);
(Continued)

(58) Field of Classification Search
None
See application file for complete search history.

(56) References Cited

U.S. PATENT DOCUMENTS 3,985,601 A * 10/1976 Panagrossi ........ A61M 25/1027
156/244.14
5,332,576 A * 7/1994 Mantelle ................ A61K 9/006
514/782
(Continued)

FOREIGN PATENT DOCUMENTS

EP 0959936 B1 6/2004
EP 2322126 A1 5/2011
(Continued)

OTHER PUBLICATIONS

International Search Report and Written Opinion, dated Apr. 17, 2018, from corresponding/related International Application No. PCT/EP2017/001314.

*Primary Examiner* — Kim M Lewis
(74) *Attorney, Agent, or Firm* — Patent Portfolio Builders PLLC

(57) ABSTRACT

A first responder device for treating blood flow from a deep wound or a bodily cavity having an inflatable balloon, a first chamber accommodating a liquid arranged for inflating the balloon, a second chamber accommodating a cooling agent capable of dissolving in the liquid when coming in contact therewith, thereby lowering the temperature, a rupturable seal between the first and second chambers, and a structure for forcing the liquid out of the first chamber into the inflatable balloon, and for rupturing the rupturable seal.

26 Claims, 8 Drawing Sheets

(51) Int. Cl.
*A61F 13/00* (2006.01)
*A61F 17/00* (2006.01)
*A61F 7/00* (2006.01)

(52) U.S. Cl.
CPC .... *A61F 17/00* (2013.01); *A61B 2017/00557* (2013.01); *A61B 2017/00654* (2013.01); *A61B 2017/00889* (2013.01); *A61B 2017/00893* (2013.01); *A61F 2007/0006* (2013.01); *A61F 2013/0054* (2013.01); *A61F 2013/00102* (2013.01); *A61F 2013/00106* (2013.01); *A61F 2013/00174* (2013.01)

(56) References Cited

U.S. PATENT DOCUMENTS

| | | |
|---|---|---|
| 6,878,142 B2 | 4/2005 | Lawrence et al. |
| 2008/0058691 A1 | 3/2008 | Sorensen |
| 2012/0109059 A1 * | 5/2012 | Ranalletta ................ A61J 1/18 604/111 |

FOREIGN PATENT DOCUMENTS

| | | | | |
|---|---|---|---|---|
| WO | 8911308 A1 | 11/1989 | | |
| WO | WO-2009114868 A1 * | 9/2009 | ......... | A61B 17/0057 |
| WO | WO-2012061140 A1 * | 5/2012 | ............ | A61M 5/007 |
| WO | 2015173264 A1 | 11/2015 | | |
| WO | WO-2016185212 A1 * | 11/2016 | .............. | A61M 5/24 |
| WO | WO-2017023499 A1 * | 2/2017 | ......... | A61B 17/1325 |
| WO | WO-2017034618 A1 * | 3/2017 | .......... | A61M 5/3137 |

\* cited by examiner

FIRST RESPONDER DEVICE

The present invention relates to a First Responder device for tamponading deep wounds, in particular (non-superficial) bullet wounds and stabbing wounds, or bleeding from body cavities, in particular, but not exclusively, bleeding noses.

TECHNICAL FIELD

From a medical perspective, bleeding from deep wounds is problematic and even dangerous, for several reasons: Among these, one is the difficulty to stop the loss of blood pressure, which may quickly lead to an ultimately fatal hypovolemic shock. Another, seemingly less immediate issue is the potential entry of harmful bacteria (or fungi, viruses, or toxins) into the wound, which bacteria (or fungi, viruses, or toxins, respectively) may cause an equally fatal septic shock with a few hours or days; and also the pain resulting from the injury.

BACKGROUND ART

A system for purging deep wounds is known from EP 0 959 936 B1, but this system is intended for the after-treatment of wounds, and is not practically useful for First Responders and paramedics. Known simple tamponades are on some occasions not considered adequate.

There is therefore still a need for providing First Responders with an adequate tool for dealing with this sort of injury, or condition, as the case may be.

SUMMARY OF THE INVENTION

To address this need, the invention provides a device for insertion into the wound or body cavity, as the case may be; whereupon the First Responder inflates a balloon inserted into the wound with a liquid comprising a cooling agent. Simultaneously, a wound cover may be expanded around the device and wound, ideally directly on the surrounding skin. Under another aspect, the invention provides a method of treating deep wounds, or bleedings from body cavities, respectively, using a cooling agent.

The expanded balloon firstly serves to seal any ruptured blood vessels by its mere presence. Secondly, the liquid containing the cooling agent, e.g. water in which a suitable agent dissolves in the process of expanding the balloon, exerts an astringent stimulus on such blood vessels. Both effects reduce the loss of blood pressure for a period of time sufficient for more professional medical help to come within reach.

In further embodiments, the outer surface of the balloon is pre-impregnated with agents assisting in the astringent action, and/or agents such as anti-bacterial agents helping in avoiding the often serious effects of a septic shock. Other medicaments may also be included, such as medicaments stabilizing vital body functions, and/or analgesics, and/or medicaments having an astringent effect.

The cooling agent is, in some embodiments, kept separate from the liquid used to inflate the balloon, in a separate chamber. When the device is actuated by the First Responder, the liquid is brought in contact with the cooling agent, which dissolves in the liquid and thereby cools down. In the process, the cooling solution inflates the balloon until same contacts the surrounding tissue sufficiently tightly for the blood to stop or to be markedly reduced. At the same time, an aseptic wound cover is expanded on the skin surface so as to bar later entry of dirt, bacteria and the like into the wound. The same effects are achieved if the blood flow comes from a bodily cavity such as the nose, vagina, or anus, rather than a bullet wound. Naturally, the device can be made in various sizes to address a variety of potential situations.

In an embodiment, a syringe as part of the device has two compartments, the proximal one of which accommodates water and the distal one of which accommodates the cooling agent. Capillary ducts enable the water to enter the second compartments only when the plunger is actuated. Once the plunger reaches the temporary wall separating the two compartments, it dislocates the temporary wall distally from its original position. Only further movement of the plunger urges the solution into the balloon and inflates it to the desired pressure.

The structure of the mechanism for expanding the wound cover is not particularly limited, as long as it keeps the cover closely attached to the elongated device until use, in an aseptic state. The structure may e.g. be pre-tensioned in an umbrella-like shape around the connection of the balloon and the lumen holding the liquid. When the liquid is pressed into the balloon, such as with a plunger, the aseptic seal is broken and the wound cover expands. After the balloon has been fully expanded, the lumen is removed from the balloon, so that the surface of the injured site is essentially flat and the surroundings covered by the expanded wound cover. This makes it easier to apply additional dressing to the wound, or padding to the bodily cavity, respectively, if required. In some embodiments, a valve is automatically closed at the same time.

In some embodiments, the balloon has an inflated shape (at a given pressure of, e.g., 1.5 bar) which is elongated, i.e. its length exceeds six times its maximum diameter.

In some embodiments, the balloon is covered with oxidized regenerated cellulose (ORC) for enhancing the hemostatic effect.

DESCRIPTION OF THE PREFERRED EMBODIMENTS

Figure 1:
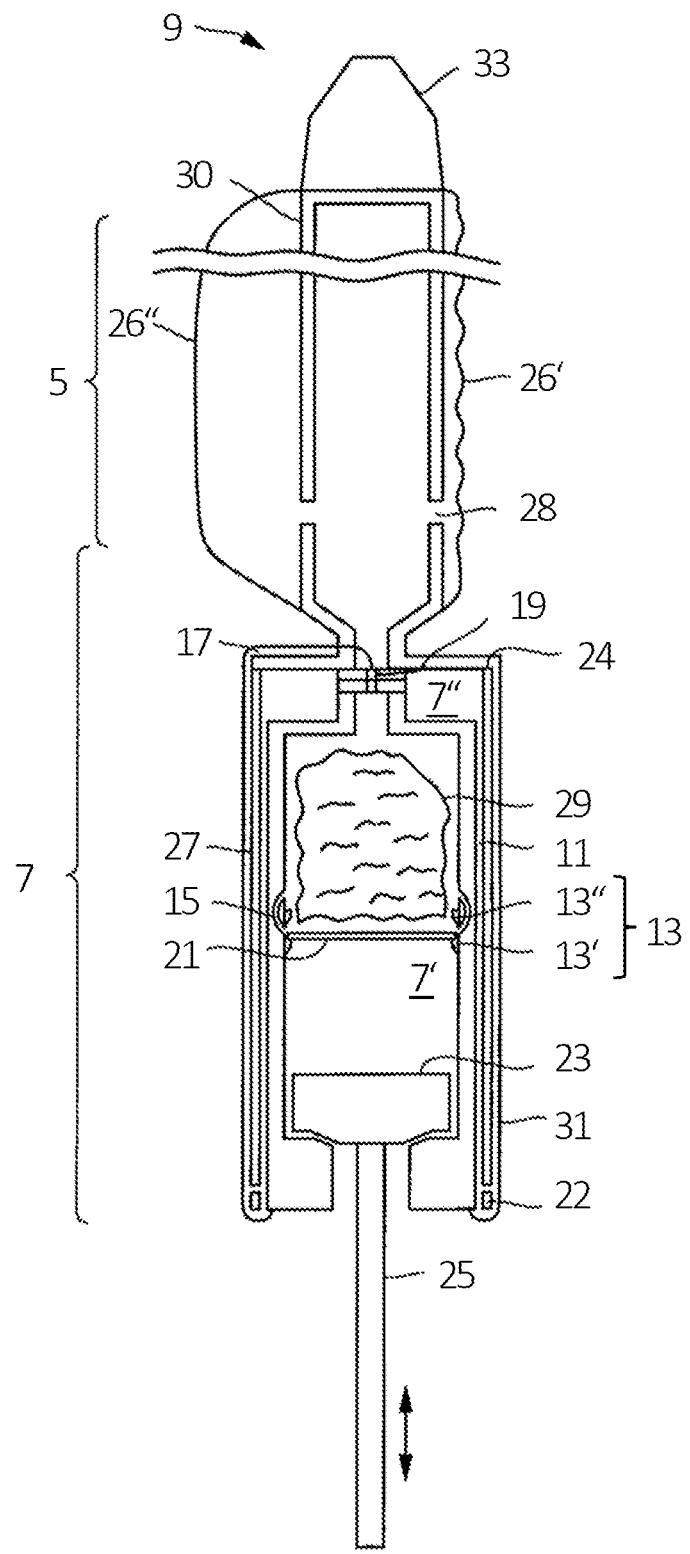
FIG. 1 shows a cross sectional view of the inventive device.

In the embodiment according to FIG. 1, the device 9 comprises a body portion 7 having a cylindrical wall 11, accommodating water in its section below (proximal to) the septum 21, and a wound cover 27 (shown only schematically) arranged around the body 7. In its section above (distally of) the septum 21, the body 7 accommodates a cooling agent 29, e.g. solid urea. The urea (or other cooling agent) may be provided in a water soluble, or water penetrable (e.g. porous) baglet.

A plunger 23, actuated via a plunger rod 25, defines a lumen of the shaft, wherein the plunger may be moved in the lengthwise direction indicated by the double-tipped arrow; i.e., inwardly (upward in FIG. 1) when activating the device, and outwardly (downward in FIG. 1) before removing the device from the wound after use. At the tip of the device 30, a soft cone (or frusto-cone, or part-ovoid) 33 of absorbing material is attached, for aid in guiding the device 9 into a deep wound, or into a body cavity, and also for providing additional absorbing capacity. Although not shown in this Figure for simplicity, the balloon 26 is also covered with an absorbing material such as oxidized regenerated cellulose, impregnated with agents such as e.g. adrenalin (epinephrine), broadband antibiotics such as e.g. tedizolid or oritavancin, and/or an analgesic such as e.g. buprenorphine.

In the embodiment shown, the device's body 7 is contiguous with a balloon section 5 arranged distally of the body 7, which balloon section comprises the inflatable balloon 26. On the right hand side of FIG. 1, the balloon is shown in its normal, non-inflated state 26'; whereas on the left-hand side of FIG. 1, the balloon is shown in its inflated state 26".

The temporary septum 21 provides a first chamber inside the body 7, accommodating the water, and a second chamber, accommodating the cooling agent. The septum 21 is held in place by distal protrusions 13', 13" formed on the inner surface of the wall and slope. Capillary ducts 15 (15a in FIG. 1a) are formed around (or between) the distal protrusions 13", so that when the plunger urges the septum 21 against the distal protrusions 13", water is pressed around the septum 21 into the distal chamber 7", thereby coming into contact with the cooling agent 29. When the plunger 23 reaches the septum 21, it dislocates same from its original position between the protrusions 13, and the solution meanwhile formed in the second chamber is urged through the valve 19 into the balloon section 5. Openings 28 are formed therein, for allowing the inflating, cool fluid to pass there through, and ultimately to exert a pressure on the balloon 26 from the inside thereof. The protrusions 13', 13" may be several (3-6), nose-like ones arranged around the perimeter; or each may be one annular protrusion, preferably resilient. Naturally, there may also be e.g. two or three part-annular protrusions on the same perimeter circle.

Figure 1A:
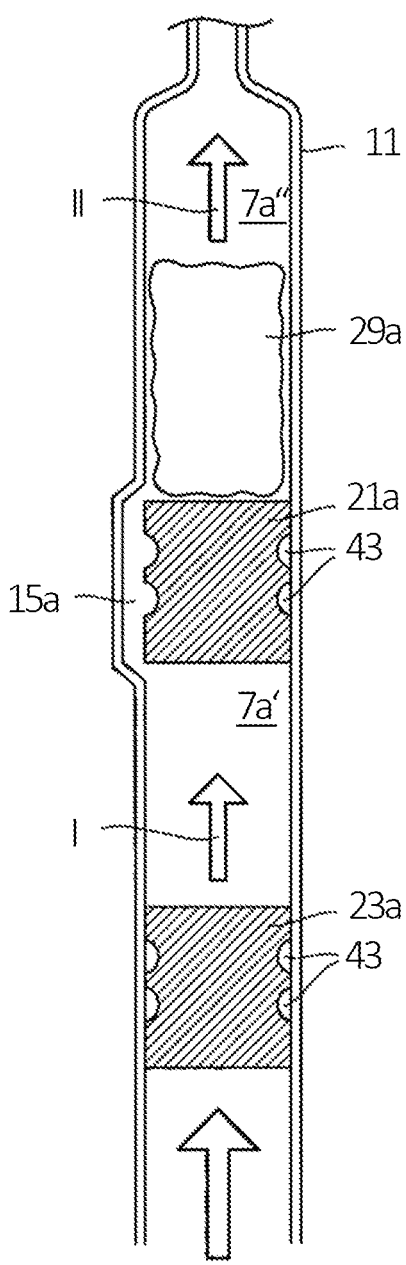
FIG. 1a schematically shows a variant of a part of the device of FIG. 1.

FIG. 1a schematically shows a variant of this structure (where appropriate, reference numerals have an "a" added): According to this example, the septum and protrusions are replaced by a second plunger-head 21a, which is held in place by plural O-rings 43 until coming into contact with the actual plunger 23a. In a first stage, actuation of the plunger (indicated by the big arrow) presses the solvent through capillary ducts 15a, which are arranged around the second plunger-head 21a, from the first chamber 7a' into the second chamber 7a" (arrow "I"), to dissolve the cooling agent placed there in a small water-dissolvable or water-penetratable bag 29a. Meanwhile, any air present in the second chamber 7a" enters into the balloon (not shown in this drawing). When the actual plunger 23a comes into contact with the second plunger-head 21a, with some additional force the second plunger-head 21a is displaced (arrow "II") from its original position towards the exit valve (also not shown in this drawing). In that second stage, the pre-cooled solution in the second chamber is pressed into the balloon as well. The actual plunger 23a in this example likewise has plural O-rings 43 as a seal against the environment. The capillary ducts 15a may be equally spaced around the original position of the perimeter of the second plunger-head 21a.

Usually, around 10 to 40 ml or even only 10 to 15 ml will be sufficient to inflate the balloon 26. For certain less deep wounds or cavities, such as bleeding from noses, less than that may be required; accordingly, a suitable volume of the lumen will generally be between 1 ml and 40 ml, preferably between 1 ml and 25 ml. In typical cases, the length of the balloon section will be more than 6 times its diameter.

Although not shown in detail, a connector arrangement may be provided at the distal end of the shaft, in order to assemble the body to the balloon section 5 described above. In this case, the septum 17 may comprise two septa in succession, wherein one septum forms part of the body section 7 (or syringe) and the other septum forms part of the balloon section 5, for sealing the balloon 26 until use. The connector assembly may consist of a male thread on the shaft part, and a matching female thread on the balloon part, or vice versa. It is envisaged to provide the various parts of the device, at least the shaft part including the plunger and the balloon part, as separate entities, which are assembled only immediately before use. The fluid may be provided in the shaft/plunger part, such as a syringe. It is envisaged to provide the cooling agent separately, but within the device body. The dissolved cooling agent is then introduced into the balloon part, inflating the balloon. Thereafter, the plunger part may be removed; to this end, it is envisioned that a valve 19 is provided, which closes automatically when the plunger part is removed. In this manner, the site remains flat, and may be covered.

In operation, the device is inserted into the wound or body cavity, such that the balloon section 5 is inside the wound or body cavity, respectively. At this stage, the balloon 26' is not yet inflated. It may be noted that the length of the device's balloon section 5 may by far exceed the diameter. In some applications, the length is about 10 to 15 cm; generally, it will usually be in the range 6 to 25 cm, while the inflated diameter is about 1 cm (if the device is not inserted into a wound—naturally, otherwise the balloon will assume a diameter to the extent the surrounding tissue allows). In this regard, the inflated diameter and length are to be measured at an inflation pressure of e.g. 1.5 bar. The balloon section, and in particular its tip section 30, allows inserting the device 9 into a deep wound by providing some stiffness, while the balloon 26 is not yet inflated.

Figure 3:
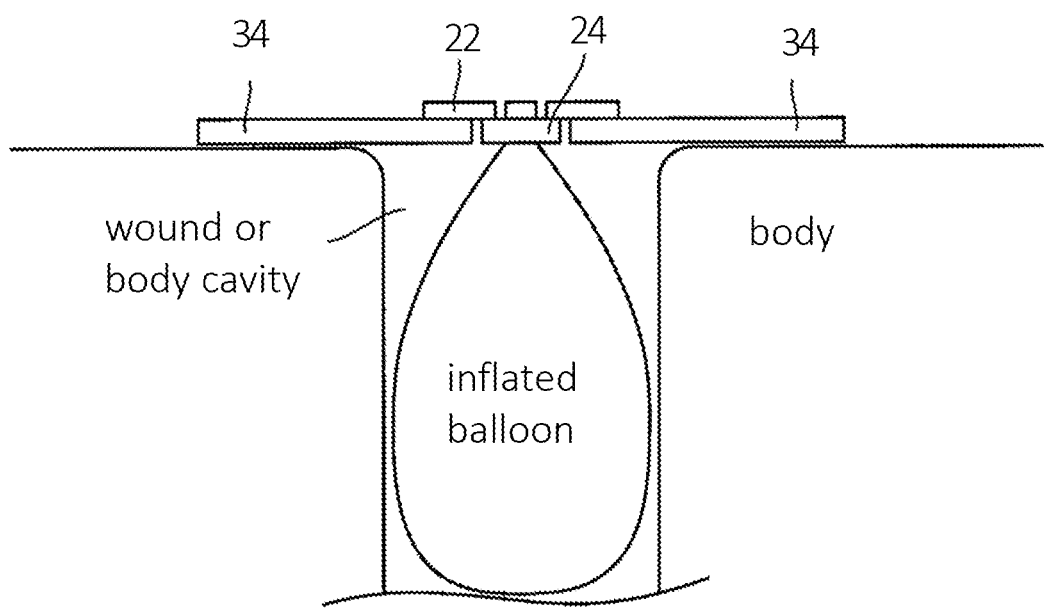
FIG. 3 schematically shows the application of the device when in use.
Figure 4:
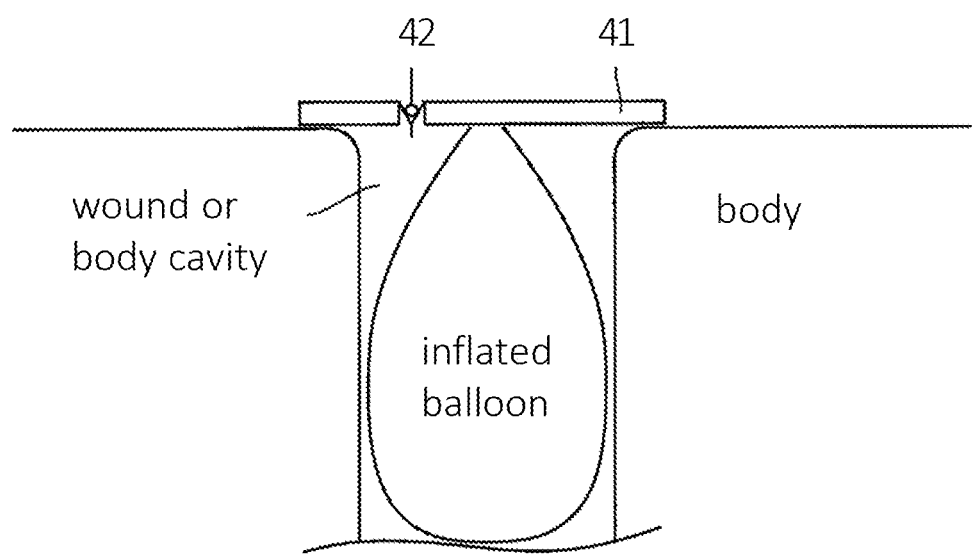
FIG. 4 depicts an embodiment similar to FIG. 3 with a valve.
Figure 5:
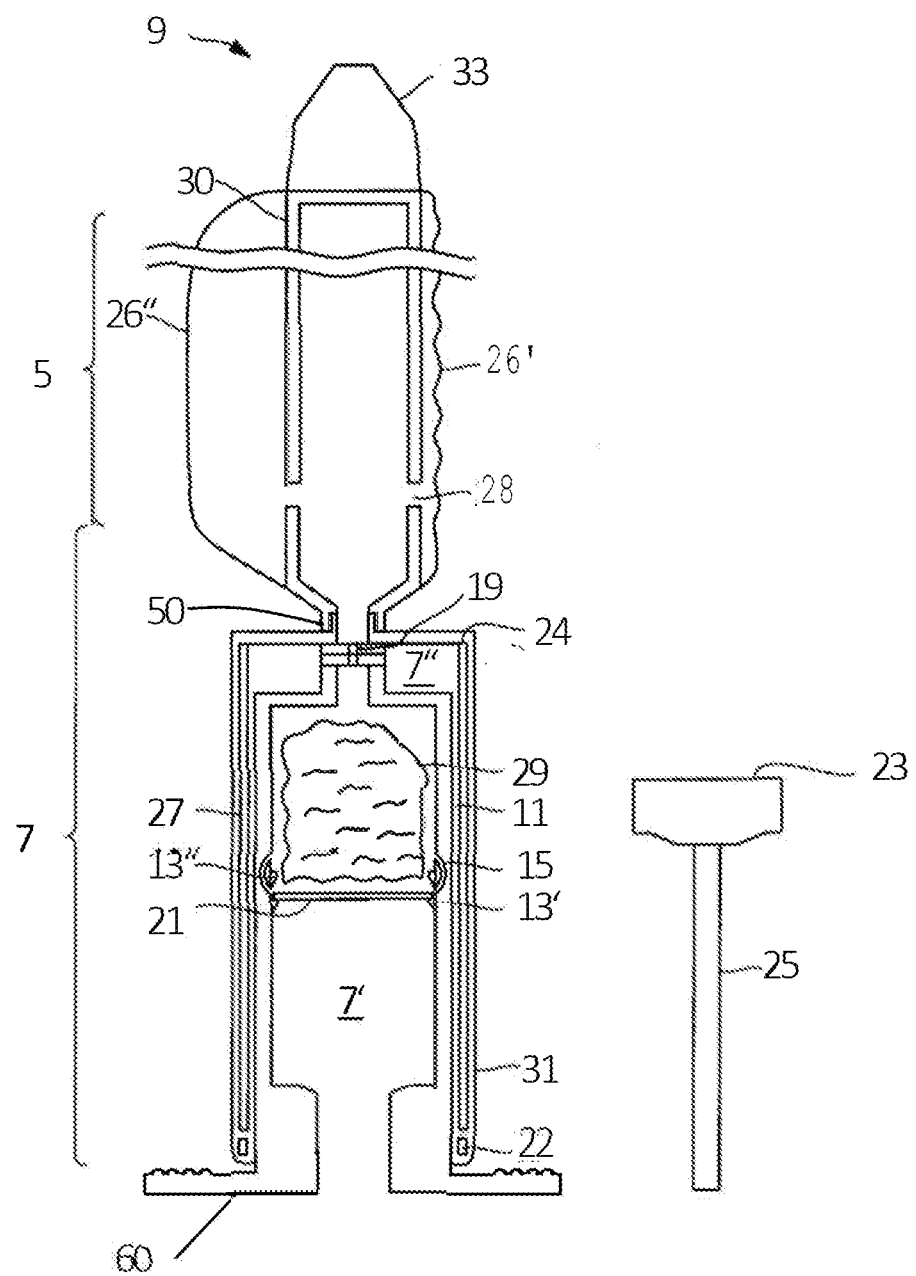
FIG. 5 depicts an embodiment similar to FIG. 1 with a lock and holder.
Figure 6:
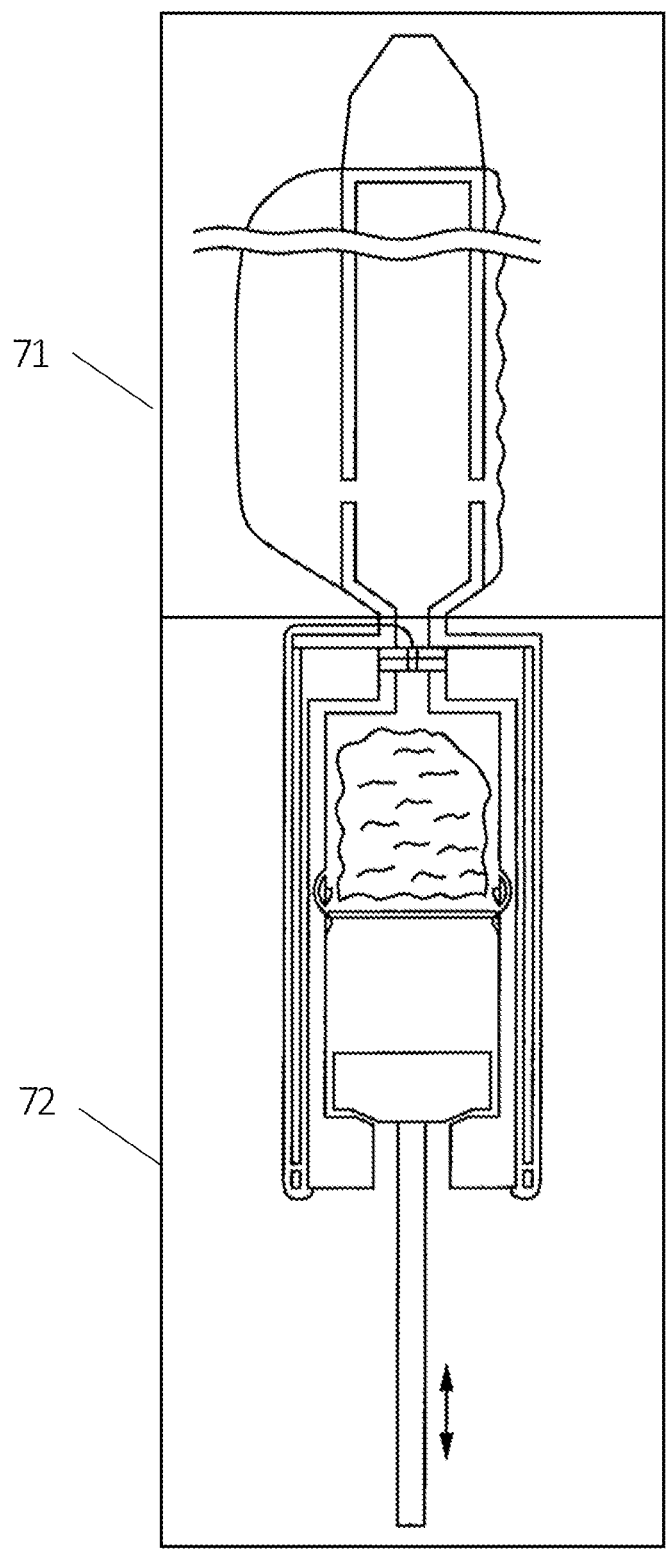
FIG. 6 depicts an embodiment similar to FIG. 1 with caps.

After insertion, the plunger 23 is displaced inwardly so as to urge the fluid contained in the first chamber around the septum 21 and into the second chamber (which in this embodiment accommodates the cooling agent 29). When the plunger is moved farther, the fluid exits also the second chamber through septum 17, into the balloon section 5, and through the openings 28 and thereby inflates the balloon 26". The balloon in this manner exerts some gentle pressure on the inside of the wound wall, helping to control bleeding. At the same time, the balloon seals the wound to prevent entry of dirt or the like. Any blood oozing out around the balloon 26 will be absorbed by the wound cover 27 expanded around the body 7 when the device is operated. It is conceivable to provide an astringent agent and/or other helpful agents, such as an anti-biotic agent, an analgesic, or an agent stabilizing circulation, on the outer surface of the balloon. The outer surface of the balloon can be covered with oxidized regenerated cellulose. Any medicaments may be impregnated thereon. FIG. 3 schematically shows how the device is arranged relative to the body under the inventive First Responder treatment.

In order for the cooling agent 29 to perform its function, it should have a positive enthalpy of solution in the fluid, i.e., under normal conditions and constant pressure, the dissolving shall readily take place, but shall require input of energy into the solution. The required energy will be provided by the thermal energy of the solvent and solute. The process will thus lead to internal cooling of the solution and therefore of the balloon 26 as a whole. Via the thin envelope of the balloon 26, the inside of the wound or body cavity will likewise be cooled, and bleeding will be slowed or stopped.

It may be estimated that an enthalpy of dissolution of more than 10 kJ/mol may be required to achieve sufficient cooling. Herein, it is assumed that an amount of between 1 g and 20 g of the cooling agent 29 may be suitably accommodated in the chamber. A suitable example is urea, which undergoes considerable cooling when coming into contact with water, in which it is well soluble. Another example is ammonium nitrate, or calcium chloride hexahydrate.

Figure 2A:
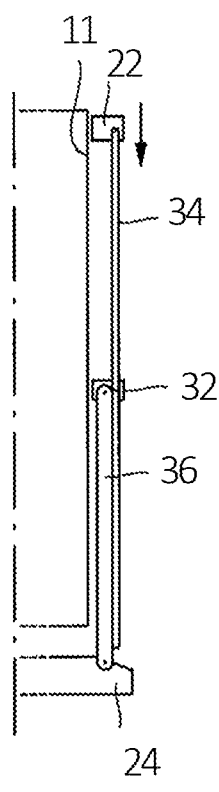
FIGS. 2a-c show another embodiment of the inventive device.
Figure 2B:
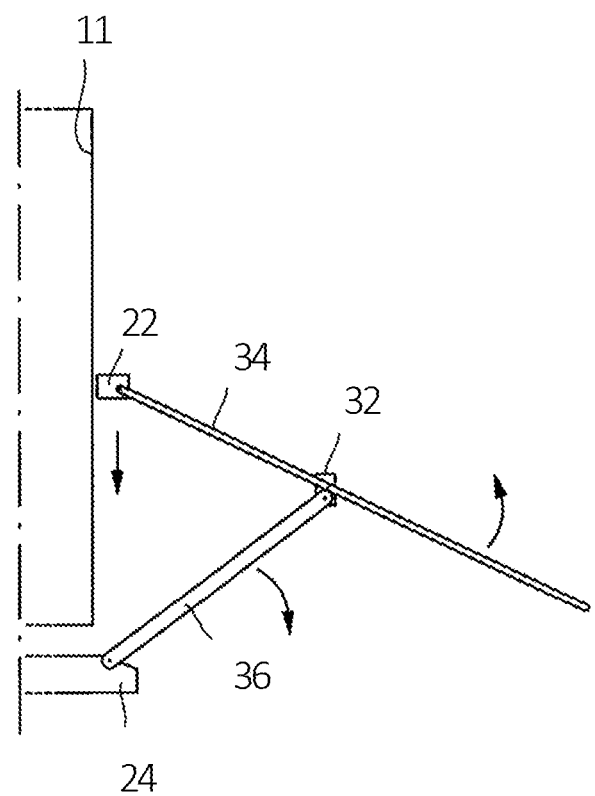
Figure 2C:
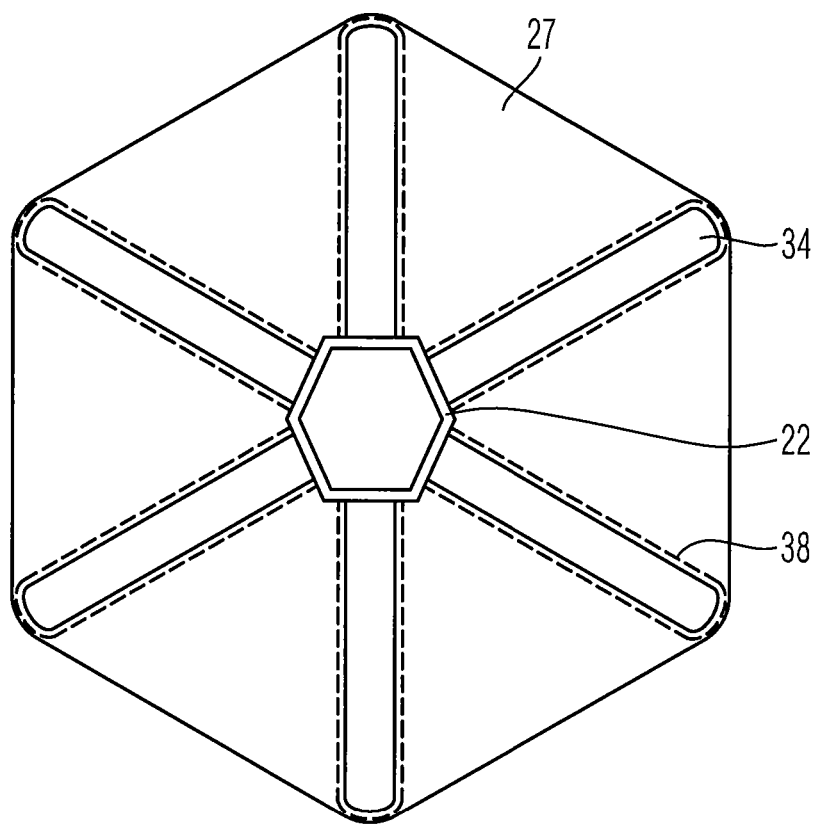

The structure employed in this example for expanding the wound cover 27 is shown schematically in FIGS. 2a-c (in which the dash-dotted line indicates the longitudinal central axis of the shaft section 7): The structure comprises a plurality of three or more radial struts 34, which in the compressed state extend lengthwise on the device 9, such as around the cavities holding the water and the cooling agent. Already in this state, the radial struts 34 are accommodated in pockets in the wound cover 27 made e.g. of oxidized cellulose. In addition, there are expansion struts 36 pivotably connected 32 to the radial struts 34 about halfway of the length of the radial struts 34. The expansion struts 36, at their distal end, are pivotably connected 24 to the device at the proximal end of the balloon section. The proximal ends of the radial struts 34 are pivotably connected to a common annular structure 22, such as a ring or polygon. This structure 22 may, but need not be fastened to the plunger rod 25. When the plunger rod 25 is actuated, or independently, the annular structure 22 presses down the top ends of the radial struts 34. Same being linked to the expansion struts 36, which in turn are supported by the fixations 24, the distal ends of the radial struts 34 move outward (see FIG. 2b), thereby gradually expanding the wound cover 27. The lengths of the struts 34, 36 and the position of the link 32 therebetween are adjusted so that when the annular structure 22 moves downward, the distal ends of the radial struts 34 move outward, from the site of the wound or body cavity, closely above the patient's skin. When the expanding motion is completed, the wound cover 27 is essentially planar and covers the periphery of the wound or body cavity, aiding in protecting the site from the ingress of dirt and the like, and at the same time aiding in absorbing any blood oozing out around the tamponade. The expansion struts 36 are preferably made as flat as possible. The joining may be made so as to pre-tension the expansion struts 36 outwards. The radial struts 34 are made sufficiently rigid to enable, e.g., pushing the outer peripheral rim of the wound cover 27 underneath any clothing present. The number of struts 34, 36 is not particularly limited, but four to eight are preferred. The entire structure including the wound cover 27, until use, is accommodated in an aseptic cover 31, which is broken only immediately before use.

FIG. 2c shows a top view (i.e., towards the patient) of a partially expanded structure: The radial struts 34 are expanding the wound cover 27, in pouches 38 of which (indicated by the dashed lines) they are accommodated. The linking of the radial struts 34 to the annular structure 22 (hexagonal in this example, for supporting six radial struts 34) is not shown in detail for simplicity. Depending on the elasticity of the wound cover material 27, there may in this state be pleats which are also not shown.

In a variant not shown, the expansion struts are not connected to the radial struts, but their outer sections are accommodated in pouches of the wound cover together with the radial struts, or in separate pouches; e.g., alternating with the pouches for the radial struts. Before use, the expansion struts are bent in a U-shape, with their outer parts extending in an opposite direction to the inner parts. When the struts are released, and/or the annular structure holding the radial struts is moved distally, the U-bent expansion struts thus help expanding the wound cover by their inherent tendency to straighten. Naturally, the outer sections of the U-bent expansion struts may also be connected to the outer parts of the radial struts, in particular if the wound cover is rather fragile.

While the invention has been described above in the context of specific embodiments, the skilled person will become aware of various suitable modifications and variations. The above description accordingly shall not be construed as limiting for the invention, which is defined by the appended claims only. More generally, the present application discloses an emergency medical device for the prophylactic or therapeutic manage-ment of hypovolemic shock, sepsis, and even pain by means of an inflatable part, in particular a balloon connected to a source of a self-cooling liquid or mixture. In other aspects, the present application discloses a method of emergency medical treatment of patients suffering from, or being threatened with, hypovolemic shock, e.g. through severe hemorrhaging, by means of inserting an inflatable device into a natural or non-natural body cavity, the device in particular having inherent cooling means.

In some variants, the First Responder device further comprises a holder 60 mounted laterally of the shaft, for keeping the device sterile until use. This holder may have a corrugated grip part for better grip, in particular if the First Responder wears gloves. The First Responder device may further include a rotatably operable lock 50 between the shaft section and/or the balloon section. It may further comprise a first cap 71 accommodating the balloon section and/or a second cap 72 accommodating the shaft section, for safer stowing the device away until use. The device may includes a hollow cylinder and a plunger movable lengthwise of the hollow cylinder, e.g., accommodated in the second cap until use. In this case, the plunger before use of the First Responder device can be accommodated beside the hollow cylinder, to be inserted into a proximal end of the hollow cylinder only for use of the device, in order to reduce the length of the stowed-away device. In some variants, the First Responder device further comprises structure 41 for providing a valve 42 between the deep wound or body cavity, and the outside, the valve capable of allowing air flow out of, but not into the deep wound or body cavity, so as to be capable of being used when there is a pneumothorax or danger thereof. The valve may in this case be made of a silicone. The balloon may likewise be made of a silicone. It may, e.g., be about 10 to 13 cm in length, and the thickness of the silicone may be in the range 0.1 to 0.3 mm, so as to be inflatable to about 25 to 40 $cm^3$ in volume.

The invention claimed is:
1. A first responder device for treating blood flow from a deep wound or a body cavity, the device comprising:
   a balloon section supporting an inflatable balloon; and
   a shaft section including:
      a first chamber accommodating a liquid arranged for inflating the balloon, and a second chamber accom- modating a cooling agent arranged for dissolving in the liquid when coming in contact therewith, thereby lowering the temperature;

a temporary seal between the first and second chambers;

a structure for forcing the liquid out of the first chamber into the second chamber, for removing or dislocating the temporary seal, and for forcing the liquid from the second chamber into the balloon; and further comprising structure for providing a valve between the deep wound or body cavity, and the outside, the valve capable of allowing air flow out of, but not into the deep wound or body cavity.

2. The first responder device of claim 1, further comprising an expandable wound cover arranged at a periphery of the device.

3. The first responder device of claim 1, wherein the length of the inflated balloon exceeds six times its diameter at a pressure of 1.5 bar.

4. The first responder device of claim 1, further comprising a releasable connector connecting the shaft section to the balloon section.

5. The first responder device of claim 4, wherein the shaft section and/or the balloon section include a rotatably operable lock.

6. The first responder device of claim 1, wherein the balloon section is in fluid communication to the shaft section through a resealing valve.

7. The first responder device of claim 1, wherein the inflatable balloon supports an absorbent material, e.g. made of oxidized regenerated cellulose, and/or a medicament such as an analgesic, an astringent agent, an agent stabilizing circulation, and/or an antibiotic agent.

8. The first responder device of claim 1, wherein the liquid is water, and the cooling agent is urea or calcium chloride hexahydrate.

9. The first responder device of claim 1, further comprising a holder mounted laterally of the shaft section.

10. The first responder device of claim 9, wherein the holder has a corrugated grip part.

11. The first responder device of claim 1, further comprising a first cap accommodating the balloon section.

12. The first responder device of claim 1, further comprising a cap accommodating the shaft section.

13. The first responder device of claim 12, wherein the plunger before use of the first responder device is accommodated beside the hollow cylinder, to be inserted into a proximal end of the hollow cylinder for use of the device.

14. The first responder device of claim 1, wherein the structure includes a hollow cylinder and a plunger movable lengthwise of the hollow cylinder.

15. The first responder device of claim 1, wherein the structure providing the valve is made of a silicone.

16. The first responder device of claim 1, wherein the balloon is made of a silicone.

17. The first responder device of claim 1, wherein a wound cover is coated or impregnated with a composition comprising adrenaline and/or an analgesic such as buprenorphine.

18. The first responder treatment of a patient, including treating blood flow from a deep wound or a body cavity of the patient, by using the first responder device of claim 1.

19. The first responder treatment of claim 18, including introducing the balloon, in a non-expanded state, into the deep wound or body cavity of the patient, and then expanding the balloon by means of the liquid.

20. The first responder treatment of claim 18, including spreading a wound cover on the body of the patient around the deep wound or the outer opening of body cavity of the patient.

21. A first responder device for treating blood flow from a deep wound or a body cavity, the device comprising:

a balloon section supporting an inflatable balloon; and a shaft section including:

a first chamber accommodating a liquid arranged for inflating the balloon, and a second chamber accommodating a cooling agent arranged for dissolving in the liquid when coming in contact therewith, thereby lowering the temperature; and an expandable wound cover arranged at a periphery of the device for expanding around the shaft section when the device is operated.

22. The first responder device of claim 21, further comprising a temporary seal between the first and second chambers; and a structure for forcing the liquid out of the first chamber into the second chamber, for removing or dislocating the temporary seal, and for forcing the liquid from the second chamber into the balloon.

23. The first responder device of claim 21, further comprising an expanding structure arranged for expanding the wound cover when in use.

24. The first responder device of claim 23, wherein the expanding structure includes 3 or more radial struts mounted on an annular structure movable with respect to the device, each optionally supported by an expansion strut pivotably connected to the device.

25. The first responder device of claim 24, wherein at least the radial struts are accommodated in pockets formed in the wound cover.

26. The first responder device of claim 21, further comprising an aseptic cover maintaining the wound cover in an aseptic state until use.

* * * * *